United States Patent [19]

Winchell

[11] 4,319,571
[45] Mar. 16, 1982

[54] OSTOMY APPLIANCE

[75] Inventor: Frank J. Winchell, Orchard Lake, Mich.

[73] Assignee: General Motors Corporation, Detroit, Mich.

[21] Appl. No.: 174,914

[22] Filed: Aug. 4, 1980

Related U.S. Application Data

[63] Continuation-in-part of Ser. No. 16,428, Mar. 1, 1979, abandoned.

[51] Int. Cl.³ .............................................. A61F 5/44
[52] U.S. Cl. ............................. 128/283; 128/DIG. 24
[58] Field of Search ........................ 128/283, DIG. 24

[56] References Cited

U.S. PATENT DOCUMENTS

| 2,563,597 | 8/1951 | Friedman | 128/283 |
| 2,583,721 | 1/1952 | Beede | 128/283 |
| 2,662,525 | 12/1953 | Priebe | 128/2 83 |
| 2,684,675 | 7/1954 | Perry | 128/283 |
| 2,808,830 | 10/1957 | Maxim | 128/283 |
| 3,483,868 | 12/1969 | Marsan et al. | 128/283 |
| 3,613,123 | 10/1971 | Langstrom | 128/295 |
| 3,780,739 | 12/1973 | Frank | 128/283 |
| 3,841,332 | 10/1974 | Treacle | 128/283 |
| 3,898,990 | 8/1975 | Nolan | 128/283 |

Primary Examiner—Robert W. Michell
Assistant Examiner—Daniel P. Burke
Attorney, Agent, or Firm—Warren D. Hill

[57] ABSTRACT

A compliant O-ring seats on the abdomen surrounding the stoma and contacting the stoma. A pouch sealing ring having an annular flange fits over the O-ring to form a sealer therewith. A waste collection pouch is secured to this sealing ring and has an opening aligned with the washer and the O-ring and a belt attached to the sealing ring secures the appliance to the body of the user.

9 Claims, 13 Drawing Figures

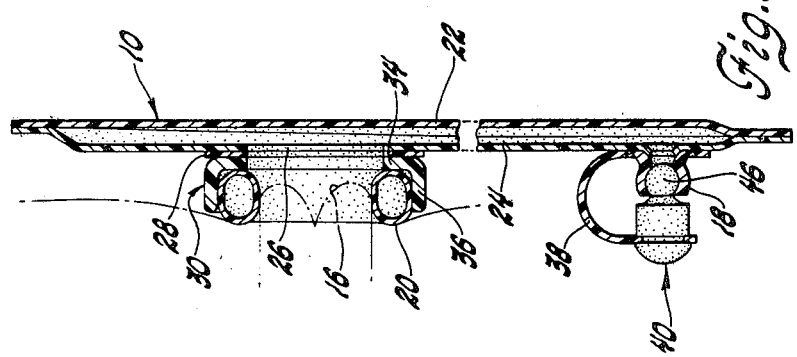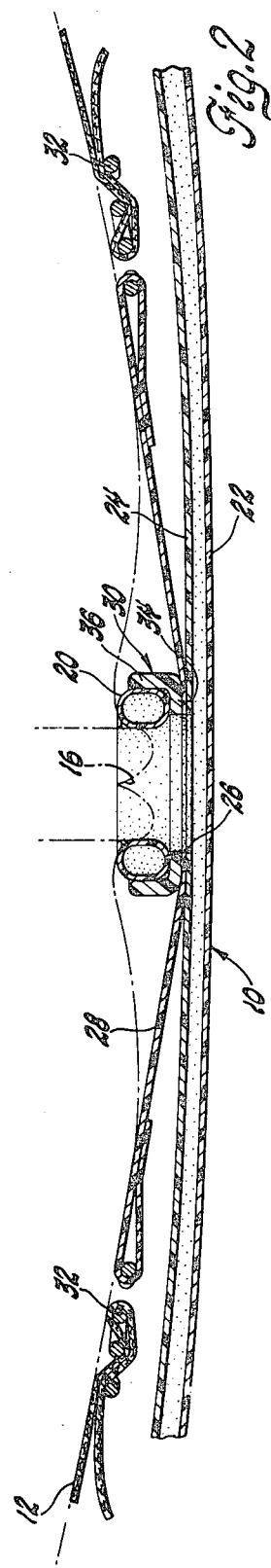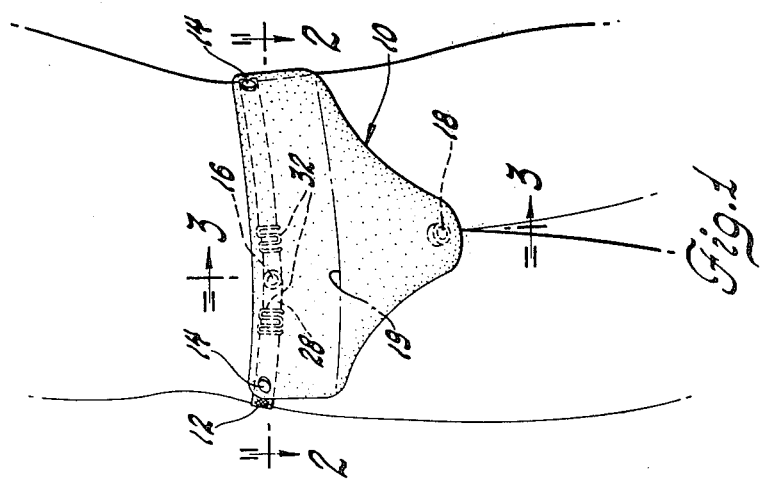

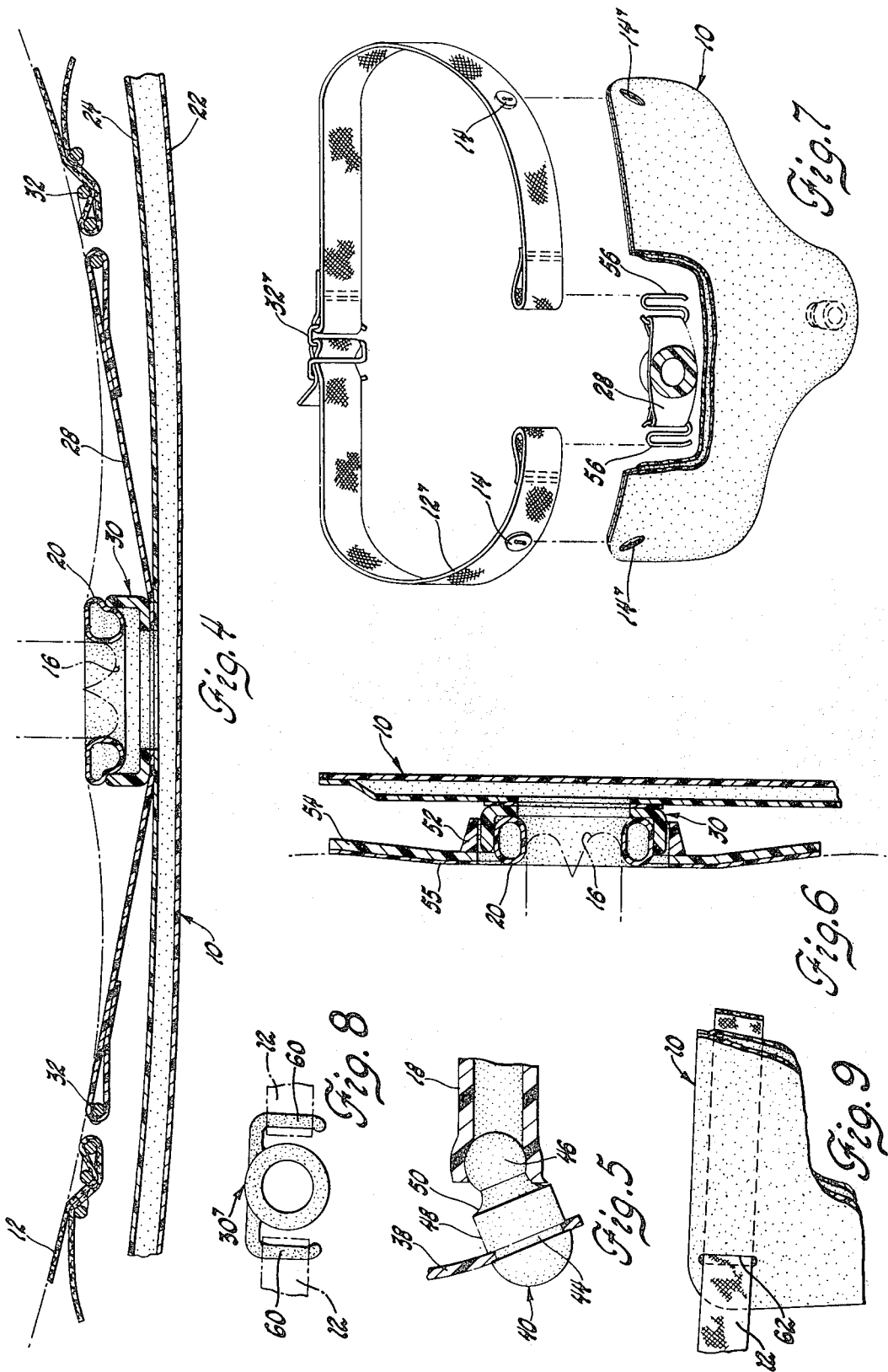

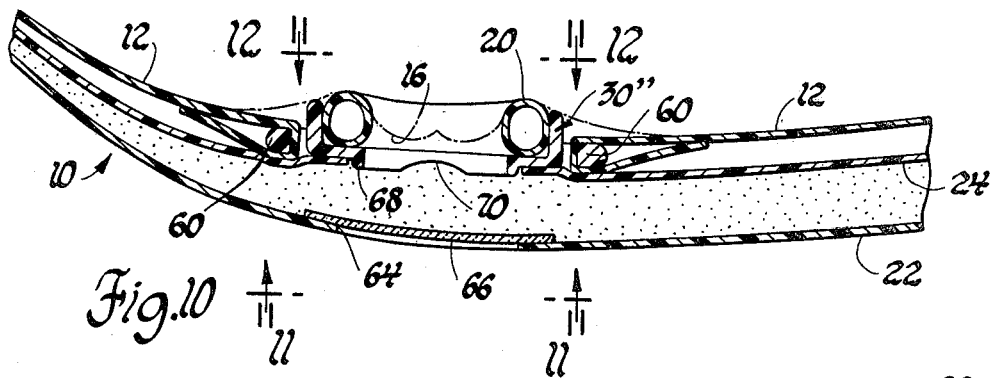
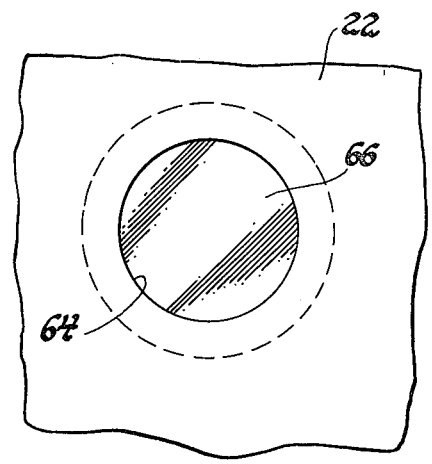
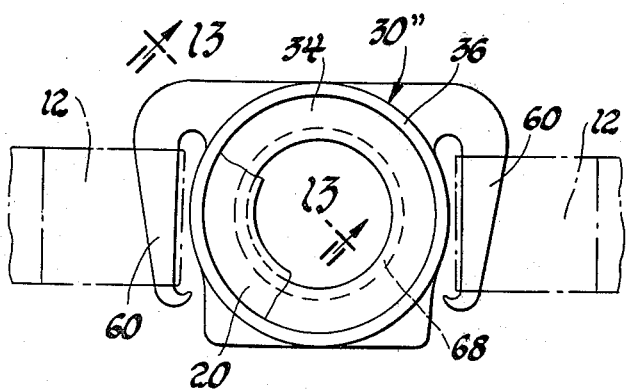
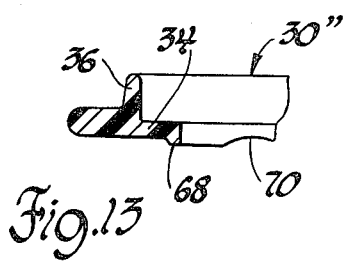

OSTOMY APPLIANCE

This is a continuation-in-part of application Ser. No. 016,428 filed on Mar. 1, 1979, now abandoned.

This invention relates to an ostomy appliance for collecting body wastes emitted from a stoma of a person having a urostomy or ileostomy.

Heretofore the ostomy appliances for collecting body wastes which were commercially successful and, therefore, available to use by the general public have been characterized by features which cause discomfort and inconvenience to the user. Such appliances, for example, require an adhesive patch on the abdomen of the user around the stoma for supporting a pouch through some retaining fixture. Those adhesive patches are directly subject to body fluids which tend to loosen the adhesive to cause leaks and further to corrode the skin to produce severe skin irritation. The collection pouches of such devices generally have inadequate capacity for overnight usage or even for many normal daytime activities. Further, such pouches tend to produce unsightly bulges under the user's clothing. Further, the nature of the attachment of the appliance to the user made it difficult to remove the appliance for cleaning or changing it.

It is, therefore, a general object of the invention to provide an ostomy appliance which requires no adhesive attachment for most of the users at least for most of their activities. It is a further object of the invention to provide such an appliance with a large waste capacity and which at the same time is readily concealed by the user's clothing. Another object of this invention is to provide such an appliance which is very easily applied or removed without discomfort or inconvenience to the user. The invention is carried out by providing an O-ring for seating against and sealing around the stoma of the user, a sealing ring in sealing engagement with the O-ring and secured to a waste collection pouch having an opening aligned with the O-ring to receive waste material from the stoma, and a belt attached to the sealing ring for securing the appliance to the body of the user and attached to the waste pouch for supporting the appliance and its contents independently of the sealing ring.

The above and other advantages will be made more apparent from the following specification taken in conjunction with the accompanying drawings wherein like reference numerals refer to like parts and wherein:

FIG. 1 is a front view of a waste collection pouch according to the invention attached to the body of the user;

FIG. 2 is a partly broken away cross-sectional view of the pouch of FIG. 1 as viewed along lines 2—2;

FIG. 3 is a cross-sectional side view of the appliance of FIG. 1 taken along lines 3—3;

FIG. 4 is a partly broken away cross-sectional view of the appliance of FIG. 1 taken along lines 2—2 illustrating the relationship of the O-ring when sealing under high pressure conditions;

FIG. 5 is an enlarged view of the drain plug during removal from the appliance;

FIG. 6 is a cross-sectional side view of the appliance of FIG. 1 illustrating an auxiliary guide ring assembly;

FIG. 7 is an exploded view of the ostomy appliance according to the invention illustrating an alternate belt attachment arrangement;

FIG. 8 is a front view of an alternate arrangement for attaching a belt to the sealing ring according to the invention;

FIG. 9 is a view of an upper corner of a pouch illustrating an alternate arrangement for attaching the pouch to the belt;

FIG. 10 is a partly broken away cross-sectional view of an ostomy appliance illustrating alternate front panel and sealing ring structures according to the invention;

FIG. 11 is a partial front view of the appliance of FIG. 10 taken along line 11—11 thereof and illustrating a transparent window in the front panel;

FIG. 12 is a partial rear view of the appliance of FIG. 10 taken along line 12—12 thereof; and FIG. 13 is a partly broken away sectional view of a sealing ring taken along line 13—13 of FIG. 12.

FIG. 1 reveals the ostomy appliance according to the invention worn by a user. A pouch 10 is secured to a belt 12 by buttons 14. The buttons 14 are each secured to a loop (not shown) which slides on the belt 12. The upper edge of the pouch 10 covers the stoma 16 in the abdomen of the user, as shown in dotted lines. The location of a drain tube 18 at the lower extremity of the pouch 10 is shown by dotted lines. The pouch is an apron style which extends across the entire width of the user's abdomen and extends straight down over about half of the abdomen and then terminates in a generally V-shaped lower portion. The broken lines 19 in FIG. 1 indicate the fluid level in the pouch when filled to the maximum capacity of typical previously available pouches. Thus, the maximum capacity of the instant pouch is far greater than the typical pouches and indeed is sufficient to permit wearing the pouch for overnight usage. The pouch configuration allows the fluid to drain away from the stoma and to avoid pressurizing the stoma whether the user is standing, supine or lying on either side. Due to the large area of the pouch, it can provide a large capacity without forming an appreciable bulge.

As shown in FIGS. 2 and 3 by cross-sectional views, the stoma 16 protruding from the abdomen of the user is surrounded by an O-ring seal 20 which sealingly engages the sides of the stoma 16 as well as the abdominal skin. The O-ring is very compliant in order to conform to the body tissues and provide a tight seal, and has a smooth surface so that it does not stick to the skin or to the mating part of the appliance. As shown, the O-ring is hollow and filled with a gas such as air or other inert fluid. A typical O-ring is generally toroidal, as shown, and is composed of hygienic latex or butyl rubber and has an outer diameter of 3.9 cm, an inner diameter of 1.9 cm and has an oval or elliptical cross-section, as shown, with diameters of 1 cm and 1.25 cm. The cross-section becomes more nearly circular when the pressures of normal usage are applied. The wall thickness is 0.5 mm although preferably the side of the ring which contacts the body is about 1.5 mm thick. Alternatively, the O-ring is composed of a solid pliant material such as a highly plasticized polyvinyl chloride (PVC). Another material for a solid O-ring is a mixture of equal parts of a silicone elastomer and silicone oil. This material is soft and pliant and continues to exude a film of silicone oil which coats the sealing ring and the skin even after repeated uses and washings.

The pouch 10 comprises an outer panel 22 and an inner panel 24 both formed of 0.2 mm thick PVC and which is heat sealed around the pouch periphery. An inlet opening 26 is formed in the inner panel and the inner panel is secured by heat sealing at the periphery of the opening 26 to a PVC strap 28 and a PVC pouch sealing ring 30. The strap 28 has left and right ends extending to stainless steel or nylon belt adjusters 32 for attachment to the belt 12. The belt preferably is a nylon reinforced elastic fabric. The strap includes an opening coincident with the inlet opening 26. The sealing ring 30 has a washer portion 34 formed of an annular ring concentric with the inlet opening 26 and has a laterally extending annular flange 36 which projects toward the abdomen of the user and is dimensioned to sealingly engage the O-ring 20 which slideably fits within the sealing ring. Due to the shape of the sealing ring, its thickness and its composition, it is substantially rigid. The cross-section thickness of the sealing ring is 1 to 1.5 mm. It is sufficiently rigid to maintain its shape even though forces much greater than those of normal usage are applied to it. The flange 36 is shorter than the O-ring cross-sectional diameter so that when the O-ring is seated in the sealing ring it protrudes beyond the flange to engage the abdomen. The inner side of the washer 34 also engages the O-ring 20 to form a seal at that point during normal usage. Thus, only the small area of the O-ring 20 between the stoma 16 and the washer portion 34 is in contact with the body waste material which flows through the inlet opening 26 into the pouch 10.

The strap 28 which is held in light tension by the belt 12 forms an angle with the plane of the washer portion 36 at the point of attachment thereto to thereby urge the sealing ring 30 and the O-ring 20 toward the abdomen to ensure the sealing contact between the O-ring 20 and the stoma 16 as well as the contact between the O-ring and the skin of the abdomen. As shown in the drawings, the pressure of the O-ring 20 against the abdomen results in a slight depression of the abdominal wall. In the event the pouch 10 becomes filled with fluid to cause an over pressure situation, the O-ring 20 acts as a piston slidable in the sealing ring. As the pouch pressure increases, the O-ring 20 is forced to slide away from the washer portion 34 as shown in FIG. 4. That action tends to push the sealing ring 30 away from the abdomen to increase the angle of the strap 28 with respect to the washer portion 34, thereby increasing the force exerted by the strap 28 on the sealing ring which force, in turn, is transferred to the O-ring 20 to increase the sealing contact to the stoma and abdominal skin to prevent leakage during the over pressure condition. Thus, the connection of the ostomy appliance to the body of the user is a dynamic one and allows a light, comfortable pressure to be applied by the belt to keep the appliance snug during ordinary conditions, however, it causes a higher pressure to be exerted when needed during high capacity conditions.

The belt coupled with the apron style pouch having widely spaced buttonholes has the advantage of wholly supporting the pouch and its contents independently of the O-ring and sealing ring assembly so that there is no downward pull on the O-ring. This allows the O-ring to remain seated around the stoma with a good seal and in comfort even though the pouch contains a large volume of fluid. The belt, wrapped around the user's waist normally passes above the hip bones and is firmly supported there near the attachment points of buttons 14. Thus the upper corners of the apron style pouch are secured to the belt at relatively high points on the abdomen near the hip bones are able to bear the full weight of the pouch contents.

Emptying of the pouch is accomplished through a drain tube 18 as shown in FIGS. 3 and 5 which is stopped by a removable polyethylene plug 40. The drain tube 18 is formed of plastic tubing, for example, sonic welded to the rear panel 24 around the periphery of a drain aperture. A lanyard 38 comprising a short polyethylene strap is also welded at the interface of the tube 18 and the pouch panel at one end or tightly fits over the tube 18 and has the other end formed in an eyelet which is engaged in a groove 44 in the outer end of the drain plug 40. The plug 40 has a spherical head 46 of larger diameter than the inner diameter of the tube 18 so that the spherical head when forced into the tubing provides a tight secure fit. An enlarged body portion 48 of the plug defines a shoulder 50 which engages the outer end of the tube 18 to provide a positioning stop. The shoulder further serves as a pivot point when the plug is tilted relative to the tube to remove the spherical head from the tube, as shown in FIG. 5. Thus, although the plug is very tightly seated in the tubing 18, it is readily removed by the tilting action. The user when emptying the pouch can remove the drain plug with one hand while using the other hand to squeeze the front panel 22 against the drain aperture to control the discharge upon plug removal.

The stoma 16 in most users is structured to protrude slightly from the abdomen and coacts with the O-ring 20 to help hold the appliance in the proper position. Thus, for most people and for most daily activities, the appliance stays in the correct position without any adhesive attachments to the skin. However, in those cases where the stoma does not protrude sufficiently to help the O-ring in place and for use during rigorous exercise, a guide ring is useful to maintain alignment with the stoma. As shown in FIG. 6, a PVC guide ring 52 mounted on an adhesive foam diaphragm 54 is secured to the skin concentrically with the stoma 16 by adhesive 55. The guide ring has an inner diameter slightly larger than the outside diameter of the sealing ring 30. The sealing ring then fits within the guide ring to provide a stable location of the appliance. Since the O-ring 20 seals around the stoma and prevents seepage of the body fluids onto the area covered by the adhesive material, the fluid cannot attack the adhesive or the skin underneath as in the case for those appliances which use the adhesive patch as a fluid interface part of the sealing system.

FIG. 7 is an exploded view of another embodiment of the ostomy appliance which differs from that described above in the configuration of the belt portion. Here the belt 12' has fixed loops to engage hooks 56 removably connected to the strap 28. A single belt adjuster 32' located at the back of the user joins two parts of the belt 12' in an adjustable fashion. Two buttons 14 are mounted on the belt parts 12' to engage buttonholes 14' formed in the pouch 10. By forming the belt 12' of elastic material, the belt can be so dimensioned that when a proper amount of tension has been applied to the belt the buttons 14 will be separated the proper distance to align with the buttonholes 14'. The spring rate of the belt between the buttons and the amount of extension required to attain the desired tension will determine the placement of the buttons on the belt. This arrangement is possible with the wide apron style pouch because the points of attachment to the belt are widely separated thereby allowing a substantial length of belt between the buttonholes for tension regulation. A typical desired belt tension is about 1.7 pounds.

In FIG. 8, another means of securing the sealing ring to the belt is shown. A sealing ring 30' has a pair of integral arms 60 secured to the top thereof and extending laterally and downwardly to form a hook at each side of the sealing ring 30' for direct attachment to fixed belt end loops. Thus, the separate strap 28 is eliminated. This embodiment is especially useful for incorporation into the FIG. 7 embodiment but is not limited to that version of the appliance. The annular portion of the sealing ring 30' has the rigidity and dimensions described above for the sealing ring 30, and the arms 60 are even thicker so that the ring will withstand belt tension more than 10 times the usual value.

FIG. 9 illustrates a vertical slit 62 in the upper corner of the pouch 10 instead of the buttonhole 14'. The slit is long enough to allow the belt 12 to be threaded through the slit thereby providing support for the pouch without using buttons. This is readily incorporated into the FIG. 1 embodiment but is not limited thereto.

A further embodiment of the ostomy appliance is illustrated in FIGS. 10-13. The belt 12 is connected directly to the arms 60 of the sealing ring 30'' as previously illustrated in FIG. 8. As in the other embodiments, an O-ring 20 slidingly and sealingly fits within the sealing ring and surrounds the stoma 16 when in place on the user's abdomen. The outer and inner panels 22 and 24 of the pouch 10 are preferably formed of an opaque PVC material in order to conceal the pouch contents for aesthetic reasons. It is, however, desirable to view the area of the stoma through the pouch particularly where the stoma is flush to assist the user in registering the sealing ring and O-ring with the stoma when installing the appliance. To allow viewing of the stoma area, a round hole 64 of say 4 or 5 cm diameter is formed in the outer panel 22 directly opposite the sealing ring 30'' and the opening is covered by a sheet of transparent PVC material 66 which is sealed to the outer panel 22 around the opening 64 to thereby form a transparent window.

The sealing ring 30'' is formed of a substantially rigid PVC material and has a pair of arms 60 at the sides for connection to the belt, a washer portion 34 and a flange 36 as described for the sealing ring 30 and in addition has an annular flange 68 extending from the inner periphery of the washer portion 34 outwardly toward the panel 22. The outer rim of the flange serves to limit movement of the outer panel 22 toward the washer portion. The rim of the flange 68 is scalloped forming arcuate depressed regions or flow vents 70 at several spaced locations around the flange. In the event the outer panel 22 is pressed against the sealing ring opening because of the sleeping position of the user or because of binding action of the user's clothing, fluid discharge from the stoma can flow through the vents 70 into the pouch thereby preventing any pressure buildup at the stoma which might occur if the outer panel were allowed to collapse against the sealing ring to form a seal around the opening of the sealing ring.

It will be apparent that many modifications to the described structure can be made within the spirit of the invention. For example, a few spot welds between the front and rear panels and distributed across the pouch help prevent bulging of the pouch.

It will thus be seen that the ostomy appliance according to this invention provides greater comfort, cleanliness and convenience and a less obtrusive bulge under the user's clothing than do other generally available ostomy appliances.

The embodiments of the invention in which an exclusive property or privilege is claimed are defined as follows:

1. An ostomy appliance for collecting body wastes emitted from a stoma in the abdomen comprising;
   a compliant toroidal O-ring for seating in sealing relationship on the abdomen surrounding the stoma, the internal diameter of the O-ring approximating the outer diameter of the stoma,
   a substantially rigid pouch sealing ring having a centrally apertured washer portion and an annular flange extending laterally from the outer periphery thereof, the sealing ring slideably fitting over the O-ring to form a sealing contact between the O-ring and both the annular flange and the washer portion,
   a waste collection pouch secured to the pouch sealing ring and having an opening aligned with the washer portion aperture whereby wastes discharged from the stoma pass through the O-ring and the pouch sealing ring into the collection pouch, and
   belt means attached to the pouch and the sealing ring for securing the appliance to the body of the user.

2. An ostomy appliance for collecting body wastes emitted from a stoma in the abdomen comprising;
   a compliant toroidal O-ring for seating in sealing relationship on the abdomen surrounding the stoma, the internal diameter of the O-ring approximating the outer diameter of the stoma,
   a substantially rigid pouch sealing ring having a centrally apertured washer portion and an annular flange extending laterally from the outer periphery thereof, the sealing ring slideably fitting over the O-ring to form a sealing contact between the O-ring and both the annular flange and the washer portion.
   a waste collection pouch secured to the pouch sealing ring, the pouch being formed in apron style having an upper portion wide enough to extend entirely across the abdomen of the user and a contiguous generally V-shaped lower portion containing discharge means, the upper portion having an opening aligned with the washer portion aperture whereby wastes discharged from the stoma pass through the O-ring and the pouch sealing ring into the collection pouch, and
   belt means attached to the pouch and the sealing ring for securing the appliance to the body of the user.

3. An ostomy appliance for collecting body wastes emitted from a stoma in the abdomen comprising;
   a waste collection pouch formed in apron style having an upper portion wide enough to extend entirely across the abdomen of the user and a contiguous generally V-shaped lower portion containing discharge means, the upper portion having an opening to receive wastes discharged from the stoma into the pouch, the upper portion having upper corners widely spaced for location at opposite sides of the user's abdomen,
   a belt attached to the widely spaced upper corners for supporting the pouch and its contents,
   a generally toroidal O-ring formed of compliant material for seating in sealing relationship on the abdomen surrounding the stoma,
   a centrally apertured annular sealing means secured to the pouch around the said opening and seated in sealing engagement with the O-ring so that wastes from the stoma pass through the O-ring and sealing means into the pouch opening, and means for fastening the sealing means to the belt to urge the sealing means and the O-ring toward the abdomen.

4. An ostomy appliance for collecting body wastes emitted from a stoma in the abdomen comprising;
   a compliant toroidal O-ring for seating in sealing relationship on the abdomen surrounding the stoma, the internal diameter of the O-ring approximating the outer diameter of the stoma,
   a substantially rigid pouch sealing ring having a centrally apertured washer portion and an annular flange extending laterally from the outer periphery thereof, the sealing ring slideably fitting over the O-ring to form a sealing contact between the O-ring and both the annular flange and the washer portion,
   a waste collection pouch secured to the pouch sealing ring, the pouch being formed in apron style having an upper portion wide enough to extend entirely across the abdomen of the user and a contiguous generally V-shaped lower portion containing discharge means, the upper portion having an opening aligned with the washer portion aperture whereby wastes discharged from the stoma pass through the O-ring and the pouch sealing ring into the collection pouch, the upper portion having upper corners, a buttonhole formed in each corner, and
   a belt formed of elastic material, buttons secured to the belt at a preset spacing when the belt is relaxed, and means for adjusting the belt so that when the buttons are aligned with the buttonholes on the pouch the belt tension is adjusted to a predetermined value established by the spring rate of the elastic belt and the belt extension required by the difference between the buttonhole spacing and the preset button spacing.

5. An ostomy appliance for collecting body wastes emitted from a stoma in the abdomen comprising;
   a compliant toroidal O-ring for seating in sealing relationship on the abdomen surrounding the stoma,
   a centrally apertured sealing means sealingly mated with the O-ring,
   a waste collection pouch secured to the sealing means, the pouch being formed in apron style having an upper portion wide enough to extend entirely across the abdomen of the user and a contiguous generally V-shaped lower portion containing discharge means, the upper portion having an opening aligned with the sealing means aperture whereby wastes discharged from the stoma pass through the O-ring and the sealing means into the collection pouch, the upper portion having upper corners, a buttonhole formed in each corner, and
   a belt formed of elastic material, buttons secured to the belt at a preset spacing when the belt is relaxed, and means for adjusting the belt so that when the buttons are aligned with the buttonholes on the pouch the belt tension is adjusted to a predetermined value established by the spring rate of the elastic belt and the belt extension required by the difference between the buttonhole spacing and the preset button spacing.

6. An ostomy appliance for collecting body wastes emitted from a stoma in the abdomen comprising;
   a compliant toroidal O-ring for seating in sealing relationship on the abdomen surrounding the stoma, the internal diameter of the O-ring approximating the outer diameter of the stoma,
   a substantially rigid pouch sealing ring having a centrally apertured washer portion and an annular flange extending laterally from the outer periphery thereof, the sealing ring slideably fitting over the O-ring to form a sealing contact between the O-ring and both the annular flange and the washer portion,
   a guide ring dimensioned to loosely fit around the pouch sealing ring including adhesive mounting means for securing the guide ring to the body of the user concentric with the stoma,
   a waste collection pouch secured to the pouch sealing ring and having an opening aligned with the washer portion aperture whereby wastes discharged from the stoma pass through the O-ring and the pouch sealing ring into the collection pouch, and
   belt means attached to the pouch and the sealing ring for securing the appliance to the body of the user.

7. An ostomy appliance for collecting body wastes emitted from a stoma in the abdomen comprising;
   a compliant toroidal O-ring for seating in sealing relationship on the abdomen surrounding the stoma, the internal diameter of the O-ring approximating the outer diameter of the stoma,
   a substantially rigid pouch sealing ring having a centrally apertured washer portion and an annular flange extending laterally from the outer periphery thereof, the sealing ring slideably fitting over the O-ring to form a sealing contact between the O-ring and both the annular flange and the washer portion,
   a waste collection pouch secured to the pouch sealing ring and having an opening aligned with the washer portion aperture whereby wastes discharged from the stoma pass through the O-ring and the pouch sealing ring into the collection pouch, and elongated slits formed in the upper corners of the pouch, and
   belt means attached to the pouch and the sealing ring for securing the appliance to the body of the user including a belt passing through the slits in the pouch to support the pouch by the upper corners.

8. An ostomy appliance for collecting body wastes emitted from a stoma in the abdomen comprising;
   a compliant toroidal O-ring for seating in sealing relationship on the abdomen surrounding the stoma, the internal diameter of the O-ring approximating the outer diameter of the stoma,
   a substantially rigid pouch sealing ring having a centrally apertured washer portion and an annular flange extending laterally from the outer periphery thereof, the sealing ring slidably fitting over the O-ring to form a sealing contact between the O-ring and both the annular flange and the washer portion,
   a waste collection pouch secured to the pouch sealing ring and having an opening aligned with the washer portion aperture whereby wastes discharged from the stoma pass through the O-ring and the pouch sealing ring into the collection pouch, the pouch including an outer panel opposite the sealing ring and subject to collapse against the sealing ring to cover the aperture therein,
   a second annular flange extending from the inner periphery of the apertured washer portion toward the outer panel and terminating in an outer rim for limiting movement of the outer panel toward the sealing ring aperture, and scallops in the outer rim forming depressions to serve as flow vents to allow the flow of wastes from the sealing ring into the pouch.

9. An ostomy appliance for collecting body wastes emitted from a stoma in the abdomen comprising;

a compliant toroidal O-ring for seating in sealing relationship on the abdomen surrounding the stoma, the internal diameter of the O-ring approximating the outer diameter of the stoma, a substantially rigid pouch sealing ring having a centrally apertured washer portion and an annular flange extending laterally from the outer periphery thereof, the sealing ring slideably fitting over the O-ring to form a sealing contact between the O-ring and both the annular flange and the washer portion, a waste collection pouch comprising front and rear panels of opaque film sealed together at their periphery to form a receptacle, the rear panel secured to the pouch sealing ring and having an opening aligned with the washer portion aperture whereby wastes discharged from the stoma pass through the O-ring and the pouch sealing ring into the collection pouch, an opening formed in the front panel aligned with the opening in the rear panel, a transparent film covering the opening and sealed around the opening in the front panel to form a window for viewing the stoma, and belt means attached to the pouch and the sealing ring for securing the appliance to the body of the user.

* * * * *